United States Patent
Turnbull

[19]

[11] Patent Number: 5,996,582
[45] Date of Patent: Dec. 7, 1999

[54] TRACHEAL ASSEMBLIES

[75] Inventor: Christopher Stratton Turnbull, Hythe, United Kingdom

[73] Assignee: Smiths Industries Public Limited Company, London, United Kingdom

[21] Appl. No.: 08/939,013

[22] Filed: Sep. 26, 1997

[30] Foreign Application Priority Data

Oct. 16, 1996 [GB] United Kingdom .................... 9621553
Oct. 18, 1996 [GB] United Kingdom .................... 9626213

[51] Int. Cl.$^6$ .................................................. A61M 16/00
[52] U.S. Cl. ............................... 128/207.29; 128/207.14; 606/172
[58] Field of Search ......................... 128/207.29, 207.14; 604/96, 36, 158, 161, 162, 163, 164, 171, 182, 264, 270, 523; 606/172

[56] References Cited

U.S. PATENT DOCUMENTS

| | | |
|---|---|---|
| 4,744,363 | 5/1988 | Hasson . |
| 5,003,657 | 4/1991 | Boiteau et al. . |
| 5,065,757 | 11/1991 | Dragisic et al. . |
| 5,178,133 | 1/1993 | Pena ........................................... 128/20 |
| 5,195,507 | 3/1993 | Bilweis ..................................... 128/20 |
| 5,199,419 | 4/1993 | Remiszewski et al. . |
| 5,263,478 | 11/1993 | Davis . |
| 5,269,769 | 12/1993 | Dhara et al. ............................. 604/264 |
| 5,308,327 | 5/1994 | Heaven et al. . |
| 5,353,784 | 10/1994 | Nady-Mohamed ........................ 128/20 |
| 5,392,774 | 2/1995 | Sato ................................... 128/207.15 |
| 5,392,787 | 2/1995 | Yoon ........................................ 128/898 |
| 5,513,627 | 5/1996 | Flam ................................. 128/200.26 |
| 5,638,813 | 6/1997 | Augustine ......................... 128/207.15 |
| 5,785,051 | 7/1998 | Lipscher et al. ................... 128/207.15 |
| 5,843,017 | 12/1998 | Yoon ........................................ 604/22 |

FOREIGN PATENT DOCUMENTS

94/03226  2/1994  WIPO .

Primary Examiner—John G. Weiss
Assistant Examiner—Joseph F. Weiss, Jr.
Attorney, Agent, or Firm—Pollock, Vande Sande & Amernick

[57] ABSTRACT

A tracheal assembly comprises an endotracheal tube and a tracheal shield. The tracheal shield has a stiff rod extending along the endotracheal tube, and a stop at the machine end of the shield which limits the extent of insertion of the shield into the tube. At its patient end, the shield has a plate or similar shield member that expands when the shield member is inserted beyond the patient end of the tube, to protect the posterior wall of the trachea during a tracheostomy procedure. The shield member can be rolled up or otherwise contracted for insertion and removal along the tube.

10 Claims, 3 Drawing Sheets

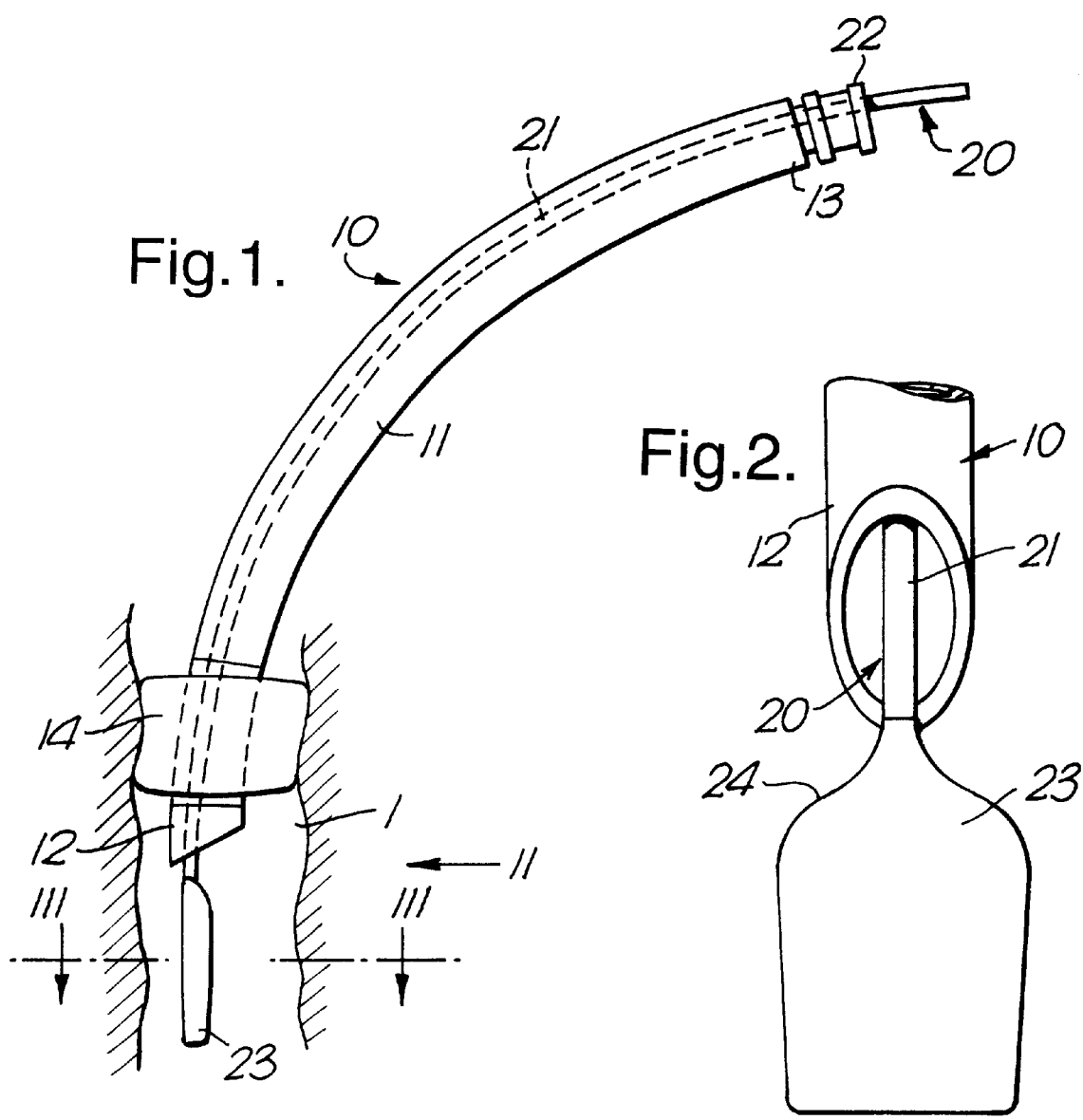
Fig.1.
Fig.2.
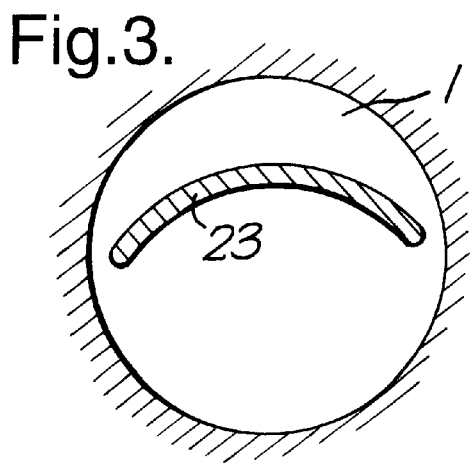
Fig.3.
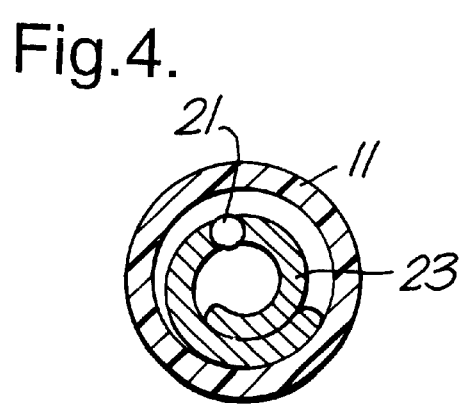
Fig.4.

TRACHEAL ASSEMBLIES

BACKGROUND OF THE INVENTION

This invention relates to tracheal assemblies.

A patient may be ventilated and supplied with anaesthetic gas via an airway in the form of an endotracheal tube inserted via the mouth or nose, the patient end being located in the trachea just below the vocal chords. In other cases, a laryngeal mask airway may be used for ventilation, the patient end of this device terminating in the region of the pharynx. Alternatively, the patient may be ventilated by means of a tracheostomy tube, the patient end of which is inserted in the trachea via a surgically made opening in the patient's neck. Tracheostomy tubes are preferable for long term use because they do not provide any obstruction in the mouth and are better tolerated by the patient. In some cases, a patient may be ventilated initially using an endotracheal tube and then by a tracheostomy tube, when it becomes apparent that the patient will need prolonged ventilation. The surgical operation needed to introduce the tracheostomy tube involves cutting through the skin and tissue over the trachea in order to make the tracheostomy. One problem with this is that, if the cut is made too deep, it can cause damage to the posterior wall of the trachea. This risk is particularly great where a percutaneous or cricothyroid puncture tracheostomy is made.

BRIEF SUMMARY OF THE INVENTION

It is an object of the present invention to provide an improved tracheal assembly.

According to one aspect of the present invention there is provided a tracheal assembly comprising an airway having a machine end arranged to project from the patient's nose or mouth, and a tracheal shield insertable within the airway, the shield having a shield member at its patient end, the shield member being expandable laterally from a first size less than or equal to the interior of the airway to a second size larger than the first size sufficient to shield the major part of the posterior wall of the trachea, such that the shield can be inserted via the airway, with the shield member projecting beyond the patient end of the airway, and so that the shield member can expand to protect the posterior wall of the trachea from damage by a tracheostomy instrument used to cut into the trachea in the region of the shield member.

The tracheal shield preferably includes a stiff rod member extending along the airway and a stop member at its machine end arranged to limit insertion of the shield by engagement with the machine end of the airway. The shield member may be a plate of a picture resistance material curved across its width, the plate being capable of being rolled along its length to the first size for insertion through the airway. Alternatively, the shield member may be a pleated fan or have several hinged petals that can be folded together for insertion and removal. In another arrangement, the shield member may have an expandable frame supporting a protective fabric. The shield member may include a spring element urging the shield member to the second size. In a further arrangement, the shield member could include an expandable balloon or be a braided member, the braided member being expanded to the second size by twisting. The airway may be an endotracheal tube or a laryngeal mask.

According to another aspect of the invention there is provided a shield for a tracheal assembly according to the above one aspect of the invention.

According to a further aspect of the present invention there is provided a tracheal shield for use with an airway, the shield having a shield member at its patient end, the shield member being expandable laterally from a first size less than or equal to the interior of the airway to a second size larger than the first size sufficient to shield the major part of the posterior wall of the trachea, such that the shield can be inserted via the airway, with the shield member projecting beyond the patient end of the airway, and so that the shield member can expand to protect the posterior wall of the trachea from damage by a tracheostomy instrument used to cut into the trachea in the region of the shield member.

A tracheal assembly and a tracheostomy method in accordance with the present invention, will now be described, by way of example, with reference to the accompanying drawings

BRIEF DESCRIPTION OF THE DRAWINGS

FIG. 1 is a partly-sectional side elevation view of the tracheal assembly in use;

FIG. 2 is a side elevation view of the patient end of the assembly along the arrow II of FIG. 1;

FIG. 3 is a transverse sectional view of the shield member along the line III—III of FIG. 1;

FIG. 4 is a transverse sectional view of the assembly during insertion of the shield member;

DETAILED DESCRIPTION OF THE PREFERRED EMBODIMENTS

Figure 5:
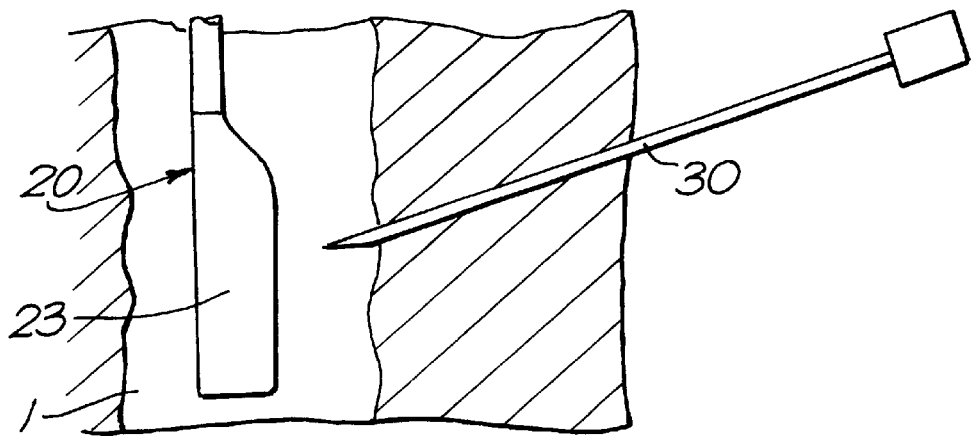
FIG. 5 is a partly sectional side elevation view showing the patient end of the tracheal assembly at a later stage of use.

With reference first to FIGS. 1 to 3, the tracheal assembly comprises an endotracheal tube 10 and a shield 20 that is slidable along the inside of the tube.

The tube 10 is a conventional oral endotracheal tube with a curved shaft 11 having a patient end 12 located in the trachea 1 and a machine end 13 with connector projecting from the patient's mouth by about 20 mm. The internal diameter of the tube is about 7 mm. An inflatable cuff 14 close to the patient end 12 of the tube 10 is inflated to seal the outside of the tube with the inside of the trachea 1 so that gas is confined to flow along the bore of the tube. The tube could, alternatively, be a nasal endotracheal tube or a laryngeal mask airway, such as of the kind described in GB 2111394.

The shield 20 comprises a curved stiff rod 21 with a stop 22 close to its machine end, which limits the extent of insertion of the shield by engagement with the machine end 13 of the endotracheal tube 10. The rod 21 may be of a stiff plastics, fibreglass, metal or similar material and has a small enough diameter to ensure that it can be easily passed into the tube 10 without substantially impeding gas flow along it. The patient end of the shield 20 has a shield member or plate 23. The plate 23 has a generally rectangular shape being about 20 mm across and about 35 mm long, the upper edge 24 of the plate being curved to a central location where the plate is attached to the rod 21. The plate 23 is about 2 mm thick and is made of a relatively stiff, resilient, puncture-resistant material such as polycarbonate, fibreglass, metal or plastics composite (such as plastic reinforced with a fibres, for example, Kevlar fibre). The edges of the plate 23 are rounded to make it atraumatic and the plate may be coated with a softer material to protect the trachea. As shown in FIG. 3, the natural shape of the plate 23 is curved across its width, with a radius of curvature of about 40 mm.

The shield 20 is used in the following way. The endotracheal tube 10 is inserted in the patient's trachea in the usual way, with its patient end 12 located below the vocal chords, and gas is administered to the patient via the tube. When it becomes apparent that the patient will require a tracheostomy, such as, for example, if he is thought to need prolonged ventilation, the cuff 14 on the tube 10 is deflated and the tube is pulled out of the patient's mouth by a distance sufficient to bring the patient end 12 of the tube level with the thyroid cartilage, to the position shown in FIG. 1. The shield 20 is then inserted to the machine end 13 of the tube 10 after having rolled up the shield plate 23 sufficiently tightly along its length to enable it to be inserted in the tube, in the manner illustrated in FIG. 4. The shield 20 is pushed into the tube 10 to its full extent, that is, until the stop 22 abuts the connector at the machine end 13 of the tube, the stop preferably being shaped or having apertures through it so that it does not substantially impede air flow along the tube. The length of the shield 20 is such that, when it is fully inserted, the shield plate 23 projects beyond the patient end 12 of the tube 10, thereby enabling the plate to unroll and expand to its natural shape, as far as it can, limited by engagement with the wall of the trachea, which typically has an internal diameter of about 23 mm. The shield 20 is oriented so that the concave surface of the plate 23 faces forwardly, or anteriorly.

Figure 6:
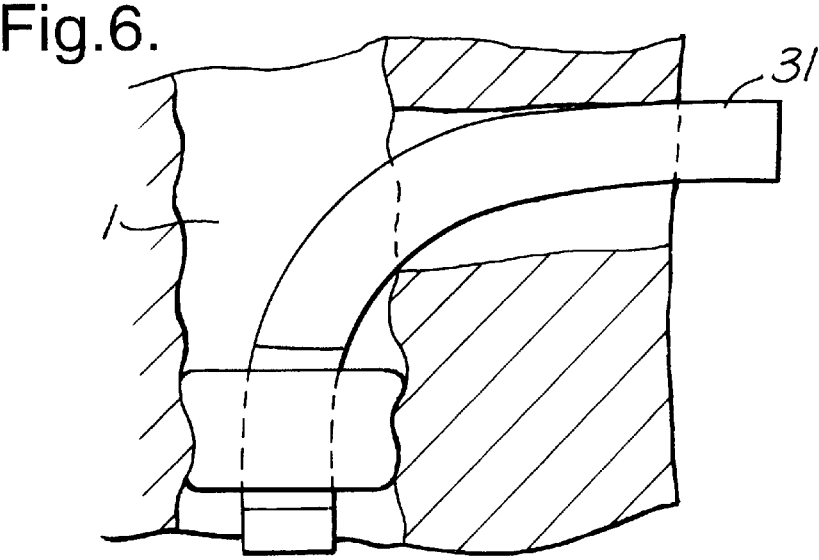
FIG. 6 is a partly sectional side elevation view illustrating insertion of a tracheostomy tube.

A percutaneous tracheostomy can then be made in the usual way, as shown in FIG. 5, by forming an incision through the skin and tissue of the neck overlying the trachea 1, in the region of the shield member, with a needle 30. The shield plate 23 protects the underlying posterior wall of the trachea 1 from damage by the needle 30, if this should be inserted too far. A guide wire is inserted through the needle 30, which is then removed, leaving the guide wire in position. The incision is enlarged using a series of dilators of increasing diameter slid along the guide wire. The shield 20 is left in place during this procedure so as to prevent the dilators damaging the posterior wall of the trachea, and is removed once the incision has been enlarged to a suitable size. The curved upper edge 24 of the shield plate 23 helps guide this back into the tube 10 and helps roll up the shield plate so that it will enter the tube. The tracheostomy tube 31 is then inserted, as shown in FIG. 6. The endotracheal tube 10 is left in the partially withdrawn position until the tracheostomy tube 31 has been correctly inserted, in case there is a problem inserting the tracheostomy tube and the endotracheal tube is needed again.

Figure 7:
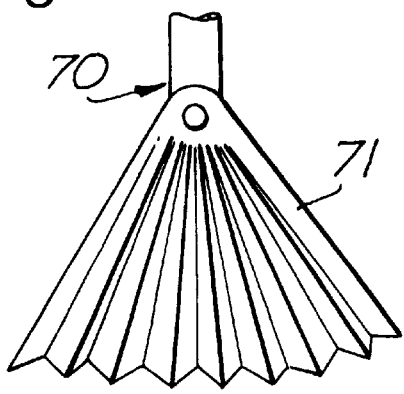
FIGS. 7 to 10 illustrate alternative shield members.
Figure 8:
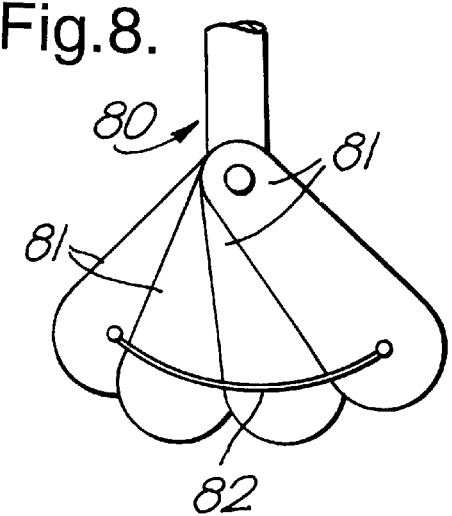
Figure 9:
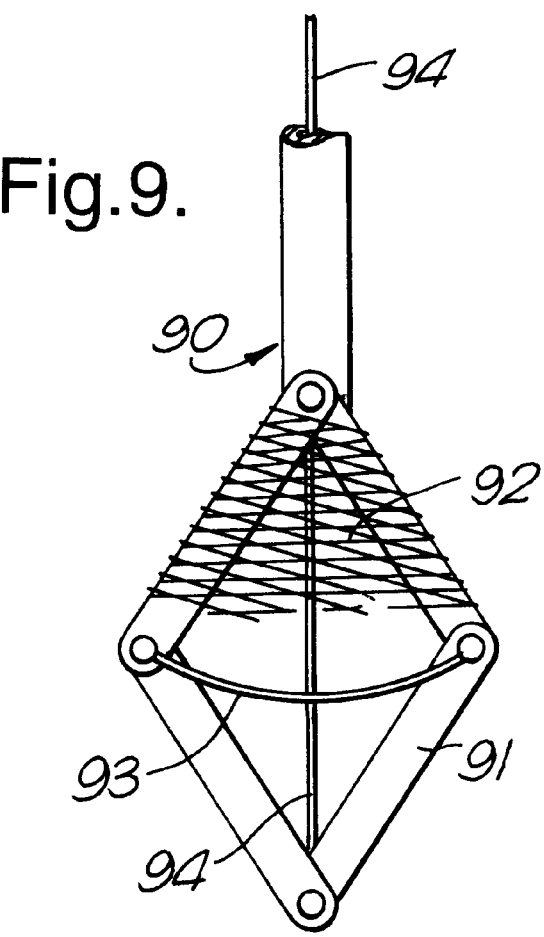
Figure 10:
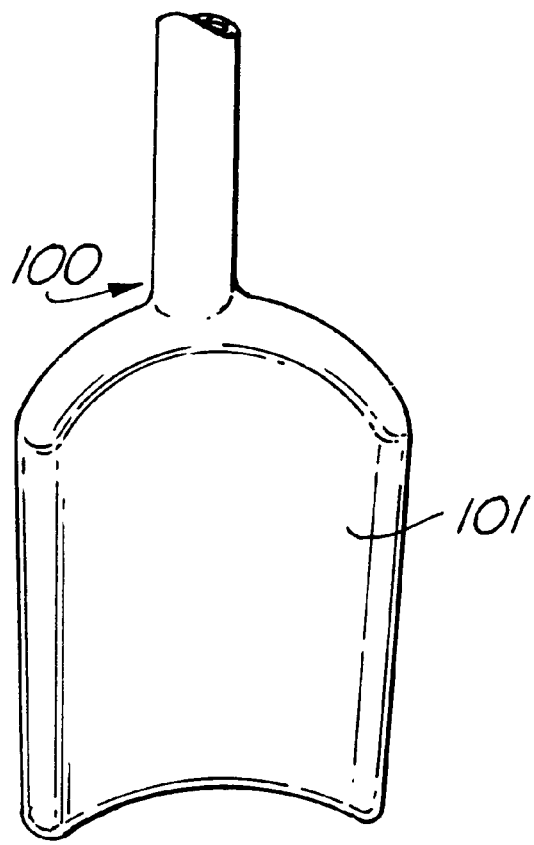

The shield member can take various different forms capable of being inserted along an endotracheal tube and expanding beyond the patient end of the tube. The shield member should not cause any significant impediment to the flow of gas along the trachea so that the patient can be ventilated via the endotracheal tube 10 until the tracheostomy has been completed. For example, as shown in FIG. 7, a shield 70 could have a shield member in the form of a pleated ruff 71 that expands like a fan. Alternatively, as shown in FIG. 8, a shield 80 could have a shield member formed by several hinged petals 81 and a spring element 82 that opens the petals outwardly when they project beyond the patient end of the tube. The petals are folded together for insertion and removal. In another arrangement, shown in FIG. 9, the shield 90 has a shield member in the form of a pantograph frame 91 supporting a protective fabric cover 92, the frame expanding laterally when it is inserted beyond the patient end of the tube either by means of a spring 93 or by a pull cord 94 extending along the rod of the shield. An alternative shield 100 could have a shield member in the form of a balloon 101 of a suitable material that can be inflated to a curved, planar shape, as shown in FIG. 10. The shield member could be a braided sleeve, net or the like that can be expanded by twisting or otherwise deforming.

What I claim is:

1. A tracheal assembly comprising: an airway having a patient end and a machine end arranged to project from a nose or mouth of a patient; and a tracheal shield insertable within and removable from said airway, said tracheal shield including an elongate member extending through said airway and a shield member at a patient end of said elongate member, said shield member being of a puncture-resistant material and being expandable laterally from a first size less than or equal to an interior volume of said airway to a second size larger than said first size sufficient to shield a major part of the posterior wall of the trachea without substantially deforming tissue of the trachea, such that said shield can be inserted and removed via said airway, said inserted shield member projecting beyond said patient end of said airway so that said shield member can expand to protect the posterior wall of the trachea from damage by a tracheostomy instrument used to cut into the trachea in a region of said shield member.

2. A tracheal assembly according to claim 1, wherein said elongate member is a stiff rod member extending along the airway, said rod member having a stop member towards the machine end of the rod member arranged to limit insertion of said shield by engagement with said machine end of said airway.

3. A tracheal assembly according to claim 1, wherein said shield member is a plate of a puncture-resistant material curved across the width of the plate, said plate being so constructed that it can be rolled along the length of the plate to said first size for insertion through said airway.

4. A tracheal assembly according to claim 1, wherein said shield member is a pleated fan.

5. A tracheal assembly according to claim 1, wherein said shield member has several hinged petals that can be folded together for insertion and removal.

6. A tracheal assembly according to claim 1, wherein said shield member has an expandable frame supporting a protective fabric.

7. A tracheal assembly according to claim 1, wherein said shield member includes a spring element, and wherein said spring element urges said shield member to said second size.

8. A tracheal assembly according to claim 1, wherein said shield member includes an expandable balloon.

9. A tracheal assembly according to any one of the preceding claims, wherein said airway is an endotracheal tube.

10. A method of performing a tracheostomy comprising the steps of: providing ventilation by means of an airway, a machine end of said airway emerging from a mouth or nose of a patient, inserting a shield through said airway until a patient end of the shield projects beyond a patient end of said airway, expanding a shield member at a patient end of said shield when it projects beyond the patient end of said airway so that said expanded shield member overlies a major part of the posterior wall of the trachea, making a tracheostomy incision in a region of said shield member while said expanded shield member protects the trachea from damage during the making of said tracheostomy incision, and inserting a tracheostomy tube through said tracheostomy incision.

* * * * *